United States Patent
Gfeller et al.

(10) Patent No.: US 9,238,319 B2
(45) Date of Patent: Jan. 19, 2016

(54) HYBRID INTERVERTEBRAL DISC SPACER DEVICE AND METHOD OF MANUFACTURING THE SAME

(71) Applicant: DePuy Synthes Products, LLC, Raynham, MA (US)

(72) Inventors: Andreas Gfeller, Basel (CH); Dirk Dittmann, Nunningen (CH); Salman Chegini, Bern (CH); Philippe Lindenmann, Basel (CH)

(73) Assignee: DePuy Synthes Products, Inc., Raynham, MA (US)

( * ) Notice: Subject to any disclaimer, the term of this patent is extended or adjusted under 35 U.S.C. 154(b) by 142 days.

(21) Appl. No.: 13/804,586

(22) Filed: Mar. 14, 2013

(65) Prior Publication Data

US 2014/0277482 A1    Sep. 18, 2014

(51) Int. Cl.
*A61F 2/44*      (2006.01)
*B29C 45/14*    (2006.01)
(Continued)

(52) U.S. Cl.
CPC ......... *B29C 45/14467* (2013.01); *A61F 2/4455* (2013.01); *A61F 2/4465* (2013.01); *B29C 45/14311* (2013.01); *A61F 2002/30004* (2013.01); *A61F 2002/30014* (2013.01); *A61F 2002/3092* (2013.01); *A61F 2002/3093* (2013.01); *A61F 2002/30777* (2013.01); *A61F 2002/30836* (2013.01); *A61F 2002/30957* (2013.01); *B29C 45/14778* (2013.01); *B29C 2045/1454* (2013.01);
(Continued)

(58) Field of Classification Search
CPC ............ A61F 2002/4475; A61F 2/442; A61F 2/4455; A61F 2/4465
USPC ....................................................... 623/17.16
See application file for complete search history.

(56) References Cited

U.S. PATENT DOCUMENTS

| 5,171,281 A | * | 12/1992 | Parsons | ................... | A61F 2/442 |
| | | | | | 623/17.15 |
| 6,569,201 B2 | * | 5/2003 | Moumene | ............... | A61F 2/447 |
| | | | | | 606/247 |

(Continued)

OTHER PUBLICATIONS

Eisner, W., "Orthofix Launches Hybrid PEEK/Titanium Spacer", Orthopedics This Week, www.ryortho.com, Jan. 14, 2013.

*Primary Examiner* — David Bates
*Assistant Examiner* — Olivia C Chang
(74) *Attorney, Agent, or Firm* — Nutter McClennen & Fish LLP

(57) ABSTRACT

A hybrid spinal implant device, and method of making the same are disclosed. The spinal implant device comprises two facing endplates, each having at least one anchoring wall or pin element, and a plastic spacer anchored to and located between the two endplates. The endplates may be manufactured from titanium. The plastic spacer may be manufactured from a radiolucent, and bio-compatible polymer-based material including polyetheretherketone ("PEEK"), polyetherketone, polyetherketoneketone, and/or fiber reinforced plastic. The endplates made of titanium allow for enhanced bone growth, while the plastic/PEEK spacer element allows for improved load absorption and distribution. The spinal implant device, using titanium endplates and a PEEK spacer, provides excellent radiolucency thereby eliminating the need for X-ray markers either intra- or post-operation. The manufacturing method for the hybrid spinal implant device uses injection molding to insert or back injection mold the spacer between the two endplates.

14 Claims, 7 Drawing Sheets

(51) Int. Cl.
  *B29L 31/00* (2006.01)
  *B29K 705/00* (2006.01)
  *A61F 2/30* (2006.01)

(52) U.S. Cl.
  CPC .. *B29C 2045/14327* (2013.01); *B29K 2705/00* (2013.01); *B29K 2871/00* (2013.01); *B29K 2995/0056* (2013.01); *B29L 2031/753* (2013.01)

(56) References Cited

U.S. PATENT DOCUMENTS

| | | | |
|---|---|---|---|
| 6,669,732 B2 | 12/2003 | Serhan et al. | |
| 7,563,284 B2 | 7/2009 | Coppes et al. | |
| 7,601,174 B2 * | 10/2009 | Kelly et al. | 623/17.13 |
| 7,621,960 B2 | 11/2009 | Boyd et al. | |
| 7,776,093 B2 | 8/2010 | Wolek et al. | |
| 7,875,075 B2 | 1/2011 | Schwab | |
| 2003/0009224 A1 * | 1/2003 | Kuras | A61F 2/442 623/17.16 |
| 2003/0045940 A1 * | 3/2003 | Eberlein | A61F 2/442 623/17.16 |
| 2003/0176925 A1 * | 9/2003 | Paponneau | A61F 2/44 623/17.16 |
| 2003/0187506 A1 * | 10/2003 | Ross et al. | 623/17.13 |
| 2006/0167551 A1 * | 7/2006 | Stad | A61F 2/4684 623/17.13 |
| 2007/0233247 A1 | 10/2007 | Schwab | |
| 2008/0015692 A1 * | 1/2008 | Heinz | 623/17.11 |
| 2008/0058939 A1 * | 3/2008 | Hughes et al. | 623/17.15 |
| 2008/0154379 A1 | 6/2008 | Steiner et al. | |
| 2009/0005708 A1 | 1/2009 | Johanson et al. | |
| 2009/0164018 A1 | 6/2009 | Sommerich et al. | |
| 2009/0187245 A1 | 7/2009 | Steiner et al. | |
| 2009/0306779 A1 | 12/2009 | Ahn | |
| 2010/0016970 A1 * | 1/2010 | Kapitan | A61F 2/442 623/17.12 |
| 2010/0094426 A1 | 4/2010 | Grohowski, Jr. et al. | |
| 2010/0125334 A1 | 5/2010 | Krueger | |
| 2010/0185292 A1 | 7/2010 | Hochshuler et al. | |
| 2014/0257492 A1 * | 9/2014 | Schwab | A61F 2/4465 623/17.16 |
| 2015/0045890 A1 * | 2/2015 | Lefebvre | A61F 2/3094 623/17.15 |

* cited by examiner

HYBRID INTERVERTEBRAL DISC SPACER DEVICE AND METHOD OF MANUFACTURING THE SAME

FIELD OF INVENTION

The present disclosure relates to spinal implant devices and methods manufacturing the same. More particularly, preferred embodiments are directed to a composite intervertebral disc spacer device that comprises a hybrid combination of two endplates, each having at least one anchoring wall or pin element, each having at least one opening therein, and a plastic spacer anchored to and in between the two endplates. Preferred embodiments are also directed to a method of manufacturing the composite intervertebral disc spacer device using an injection mold process to form the plastic spacer between the two endplates.

BACKGROUND

Many different medical procedures are performed that require the stabilization of adjacent bone sections or bone portions through the securing of an interbody spacer to the adjacent bone portions. Examples of these spacers are known to those in the field as interbody cages, corpectomy cages, osteotomy wedges, joint spacers, and bone void fillers, among other names and labels.

As one example, spacers are used to fuse bone joints. Spacers are also used to repair complex fractures where bone is missing and in bone regions where there are voids within the bone structure, such as when a tumor and adjacent bone may be removed. Spacers are also used in the performance of osteotomies by placing the spacers between adjacent bone portions to perform a wedging action, including to straighten a bone. These are but a few examples of, and are an not exhaustive description of the medical procedures that require the placement of a spacer between adjacent bone portions.

In each procedure, the spacer placed between the bone portions is required to be rigidly joined to the adjacent bone portions. A multitude of different apparatus have been designed for this joinder purpose. One example of connecting or joining a spacer to adjacent bone structure is through the use of insertion screws. While screws are generally effective for this purpose, they are limited in the sense that they do not afford stability in all orthogonal dimensions often required to effect the optimal or desired rigidity.

Spacers are also commonly used in spinal repair and reconstruction. The spine is a flexible column formed of a plurality of bones called vertebra. Each vertebrae are annular-shaped structures having a hard cortical bone on the outside and porous cancellous bone on the inside. The vertebrae are stacked, in column fashion, one upon the other, forming a strong annular column supporting the cranium and trunk. The core of the spine protects the nerves of the spinal cord. The different vertebrae are connected to one another by means of articular processes and intervertebral, fibro-cartilaginous bodies.

The intervertebral fibro-cartilages are also known as intervertebral disks and are made of a fibrous ring filled with pulpy material. The disks function as spinal shock absorbers and also cooperate with synovial joints to facilitate movement and maintain flexibility of the spine. When one or more disks degenerate through accident or disease, nerves passing near the affected area may be compressed and are consequently irritated. The result may be chronic and/or debilitating back pain. Various methods and apparatus have been designed to relieve such back pain, including spinal fusion using a suitable graft or interbody spacer using techniques such as Anterior Lumbar Interbody Fusion ("ALIF"), Posterior Lumbar Interbody Fusion ("PLIF"), or Transforaminal Lumbar Interbody Fusion ("TLIF") surgical techniques. The implants used in these techniques, also commonly referred to as an intervertebral spacer, are placed in the interdiscal space between adjacent vertebrae of the spine.

Ideally, a fusion grant should stabilize the intervertebral space and become fused to adjacent vertebrae. Moreover, during the time it takes for fusion to occur, the graft should have sufficient structural integrity to withstand the stress of maintaining the intervertebral space without substantially degrading or deforming. The graft should also have sufficient stability to remain securely in place prior to the time of actual bone ingrowth fusion.

One significant challenge to providing fusion grant stability (prior to actual bone ingrowth fusion) is preventing spinal extension that may result during patient movement. Distraction of the vertebral space containing the fusion graft may cause the graft to shift or move, which in turn may result in disrupting bone ingrowth fusion and causing pain.

Current and existing spinal fusion technology has been limited, and is lacking in certain respects relating to the above described issues. Among the limitations of certain of these systems is the requirement that complicated steps need to be performed to accomplish their proper use. As noted, others of these type of devices and systems, included screws, and lack the optimal multi-dimensional stability, while others are less than desirable because they use components that may project externally of one or more of the bone portions between which the spacer is located. Other deficiencies and problems also exist with respect to prior devices and systems.

The systems that rely upon the use of screws may have certain limitations. Such systems may not effectively allow compression forces to be generated between the spacers and adjacent bone portions. Further, while the screws do stabilize the bone-spacer junction in one plane, that is normally flexion-extension, they may not, in certain applications, control bending in another plane or direction that is orthogonal to the plane of the screw.

A further problem with existing systems is that components or parts typically are often not locked in place and are thus prone to working loose over time. Screws, for example, may loosen over extended usage and time in the absence of incorporating some structure that effectively prevents turning or lengthwise movement. Without such locking elements, a loosened screw could result in partial or full separation of the device from the bone portions and/or spacers that they penetrate.

Several disc spacer devices have been designed and proposed to address some of these noted limitations. Examples include U.S. Pat. No. 6,569,201 for a Hybrid Composite Interbody Fusion Device, issued to Moumene et al.; U.S. Pat. No. 7,776,093 for a Vertebral Body Replacement Apparatus And Method, issued to Wolek et al.; and U.S. patent application Ser. No. 11/643,994 for an Interbody Fusion Hybrid Graft. In addition to these devices, the medical field is constantly seeking system designs that might be efficiently and consistently installed and that, most significantly, will affect the desired fusion in a manner that will be safe and reliable for the patient. The various embodiments of devices and methods described in this application address such a need.

SUMMARY

The above noted problems, which are inadequately or incompletely resolved by the prior art are completely addressed and resolved by the presently described embodiments of devices and methods.

A preferred embodiment of the device is a hybrid spinal implant for positioning at an intervertebral space and comprising a first end plate, configured for fitting within a disc space, wherein the first end plate comprises a first surface for engaging a first vertebral surface and a second surface opposite the first surface, wherein the second surface comprises at least one anchoring protrusion; a second end plate configured for fitting within a disc space, wherein the second end plate comprises a first surface for engaging a second vertebral surface and a second surface opposite the first surface, wherein the second surface comprises at least one anchoring protrusion; a unitary plastic spacer formed through injection molding and positioned between the first and second end plates and anchored to the first and second end plates respectively by each of the at least one anchoring protrusions.

Another preferred embodiment of the device is a hybrid spinal implant for positioning at an intervertebral space, comprising a first end plate, configured for fitting within a disc space, wherein the first end plate comprises a first surface for engaging a first vertebral surface and a second surface opposite the first surface, wherein the second surface integrally comprises a plurality of wall and pin protrusions; a second end plate configured for fitting within a disc space, wherein the second end plate comprises a first surface for engaging a second vertebral surface and a second surface opposite the first surface, wherein the second surface integrally comprises a plurality of wall and pin protrusions; a unitary ring-shaped plastic spacer formed through injection molding and positioned between the first and second end plates and anchored to the first and second end plates respectively by each of the plurality of wall and pin protrusions.

A further preferred embodiment of the hybrid bone implant for positioning within a bone structure cavity, comprises a first end plate, configured for fitting within a bone structure cavity, wherein the first end plate comprises a first surface for engaging a first bone surface and a second surface opposite the first surface, wherein the second surface comprises at least one anchoring protrusion; a second end plate configured for fitting within a bone structure cavity, wherein the second end plate comprises a first surface for engaging a second bone surface and a second surface opposite the first surface, wherein the second surface comprises at least one anchoring protrusion; a unitary ring-shaped plastic spacer formed through injection molding and positioned between the first and second end plates and anchored to the first and second end plates respectively by each of the at least one anchoring protrusions.

A preferred embodiment for a method for manufacturing a hybrid spinal implant, where the hybrid spinal implant is for placement in an intervertebral space, is a method comprising the steps of (a) positioning within an injection mold tool a first end plate, said first end plate configured for fitting within a disc space, wherein said first end plate comprises a first surface for engaging a first vertebral surface and a second surface opposite the first surface, wherein the second surface comprises at least one anchoring protrusion; (b) positioning within said injection mold tool a second end plate opposite and spaced away from said first end plate, wherein said second end plate comprises a first surface for engaging a second vertebral surface and a second surface opposite the first surface, wherein the second surface comprises at least one anchoring protrusion; (c) forming a unitary plastic spacer between the first and second end plates by injection molding wherein the plastic spacer is anchored to the first and second end plates respectively by each of the at least one anchoring protrusions.

The various embodiments will be best understood by reading the following detailed description of the several disclosed embodiments in conjunction with the attached drawings that briefly described below.

BRIEF DESCRIPTION OF THE DRAWINGS

The above-mentioned and other features and advantages of embodiments of the devices, and the manner of attaining them, will become more apparent and will be better understood by reference to the following description of embodiments taken in conjunction with the accompanying drawings, wherein corresponding reference characters indicate corresponding parts throughout the several views and wherein.

DETAILED DESCRIPTION OF PREFERRED EMBODIMENTS

Figure 1:
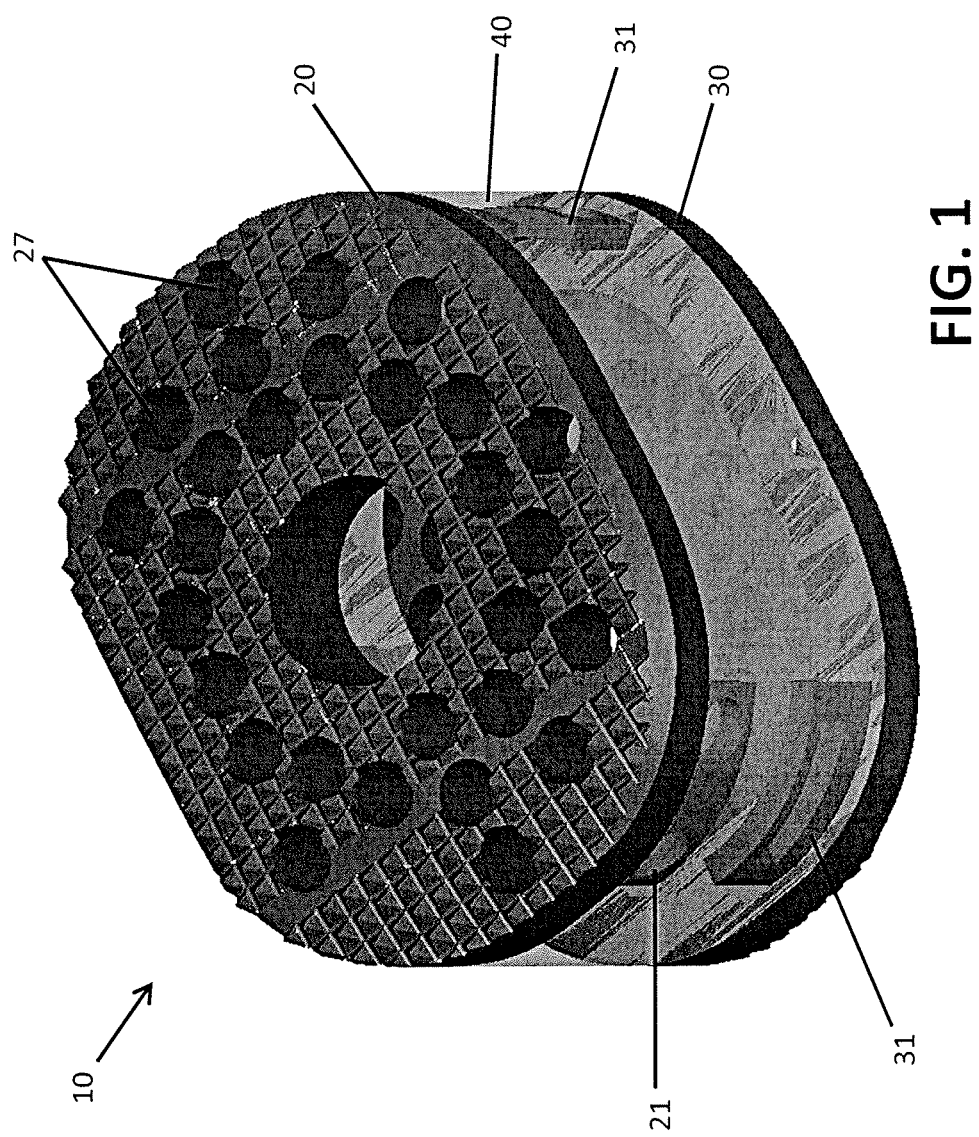
FIG. 1 shows an isometric view of an embodiment of the hybrid intervertebral disc spacer.

In the following detailed description, reference is made to the accompanying drawings wherein like numerals designate like parts throughout, and in which is shown, by way of illustration, the disclosed embodiments may be practiced. It is to be understood that other embodiments may be utilized and structural or logical changes may be made in alternate aspects. Therefore, the following detailed description is not to be taken in a limiting sense, and the scope of the disclosed embodiments is defined by the appended claims and all of their equivalents.

Moreover this detailed description is intended to be read in connection with the accompanying drawings, which are to be considered part of the entire written description of the preferred embodiments. The drawing figures are not necessarily to scale and certain features of the embodiments and examples may be shown exaggerated in scale or in somewhat schematic form in the interest of clarity and conciseness. In the description, relative terms such as "horizontal," "vertical," "up," "down," "top," "bottom," "outer," "inner," "front," "back," "anterior," and "posterior," as well as derivatives thereof (e.g., "horizontally," "downwardly," "upwardly," etc.) should be construed to refer to the orientation as then described or as shown in the drawing figure under discussion. These relative terms are for convenience of description and normally are not intended to require a particular orientation.

Further, terms including "inwardly" versus "outwardly," "upwardly" versus "downwardly," "longitudinal" versus "lateral" and the like are to be interpreted relative to one another or relative to an axis of elongation, or an axis or center of rotation, as appropriate. Terms concerning attachments, coupling and the like, such as "connected" "interconnected,"

"coupled," "engaged" and "attached" refer to a relationship wherein structures are secured or attached to one another either directly or indirectly through intervening structures, as well as both movable or rigid attachments or relationships, unless expressly described otherwise.

In certain embodiments, the intervertebral spacer implant device may be employed to maintain appropriate spacing between adjacent vertebrae, for example, where wear or injury has led to the need for disc replacement. In other embodiments, the intervertebral spacer implant device may be configured for both disc and vertebrae replacement. Regardless, embodiments of the described devices provide a spinal fusion device that provides column support to the spine and facilitates a fusion between adjacent vertebral bodies.

In certain embodiments, as shown in the attached drawings, the fusion spacer device includes three elements, namely, a pair of endplates designed and configured to be attached to respectively upper and lower vertebrae surfaces, and a vertebral plastic disc spacer in between the two endplates. More particularly, as shown in FIG. 1, in a preferred embodiment, the disc spacer 10 includes an upper endplate 20 and a lower endplate 30 that sandwiches a plastic spacer element 40. The assembly or construction of the disc spacer provides, in a preferred embodiment, that the plastic spacer element is back injection molded after the endplates 20 and 30 are placed within an injection molding tool. Through use of back injection molding, the plastic spacer element 40 is formed to precisely the desired shape, and ensures complete contact between the surfaces of the spacer element with the respective upper endplate 20 and lower endplate 30. In a preferred embodiment, as shown and described in more detail below, plastic spacer element is formed generally in a cylindrical shape.

The isometric view shown in FIG. 1 illustrates the plastic spacer element 40 as translucent to further show the location of anchoring elements to lock the relative position of the upper endplate 20 and lower endplate 30 with the spacer element 40. The anchoring elements shown in FIG. 2, in a preferred embodiment, are wall protrusions 21, integral with upper endplate 20, and wall protrusions 31, integral with lower endplate 30.

Figure 2:
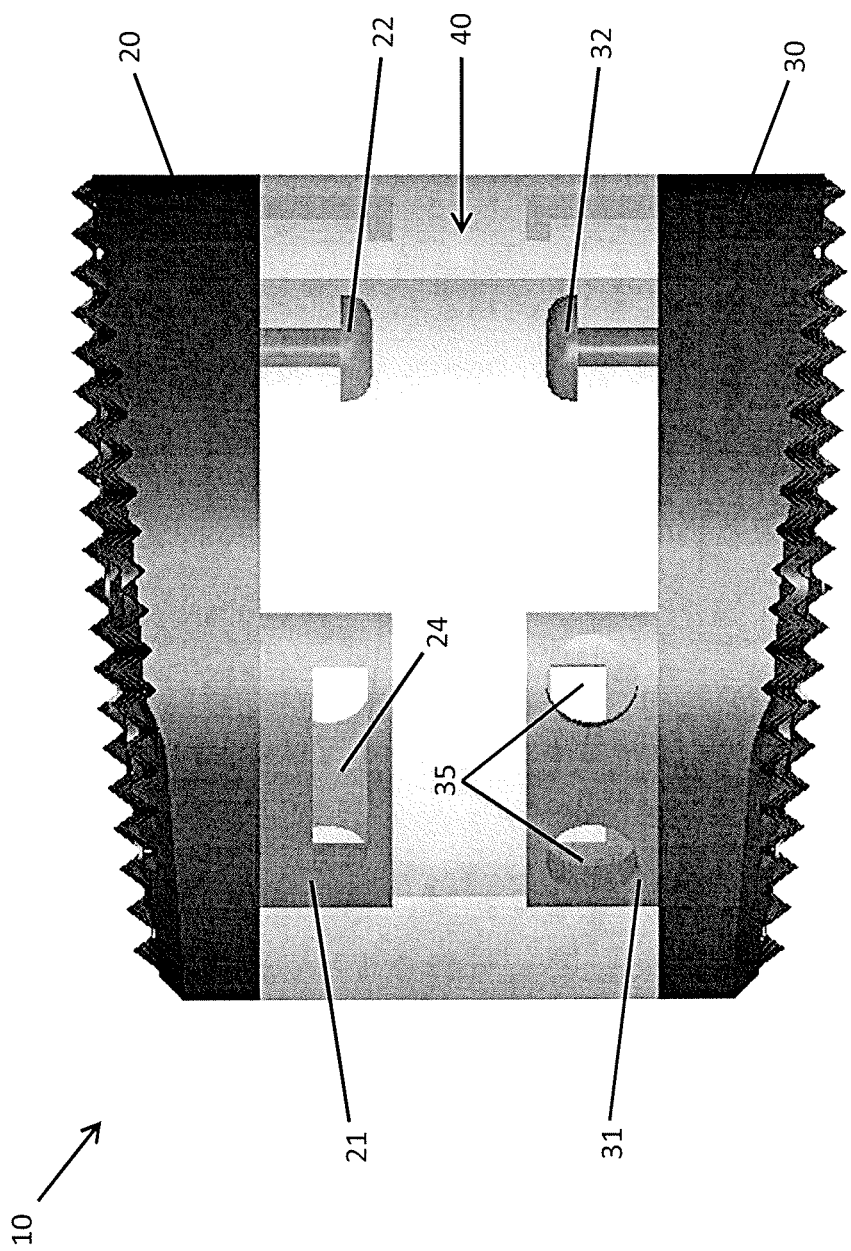
FIG. 2 shows a side view of an embodiment of the hybrid intervertebral disc spacer.

FIG. 2 shows a side-view of a preferred embodiment of the disc spacer 10, again with the plastic spacer element 40 shown as translucent to illustrate example anchoring elements. In addition to the wall protrusions 21 and 31, which are integrally attached to the upper endplate 20 and lower endplate 30, respectively, FIG. 2 shows use of pin protrusions 22 and 32, which are similarly attached to the upper endplate 20 and lower endplate 32. The pin protrusions shown in FIG. 2 are a T-shape, and are completely surrounded by the spacer element 40. In view of the imbedded placement of the T-shaped pin protrusions 22, 32 within the back injection formed spacer element 40, such protrusions provide both lateral stability and further reduce the possible separation or delamination of either endplate 20, 30 from the spacer element 40.

Figure 3:
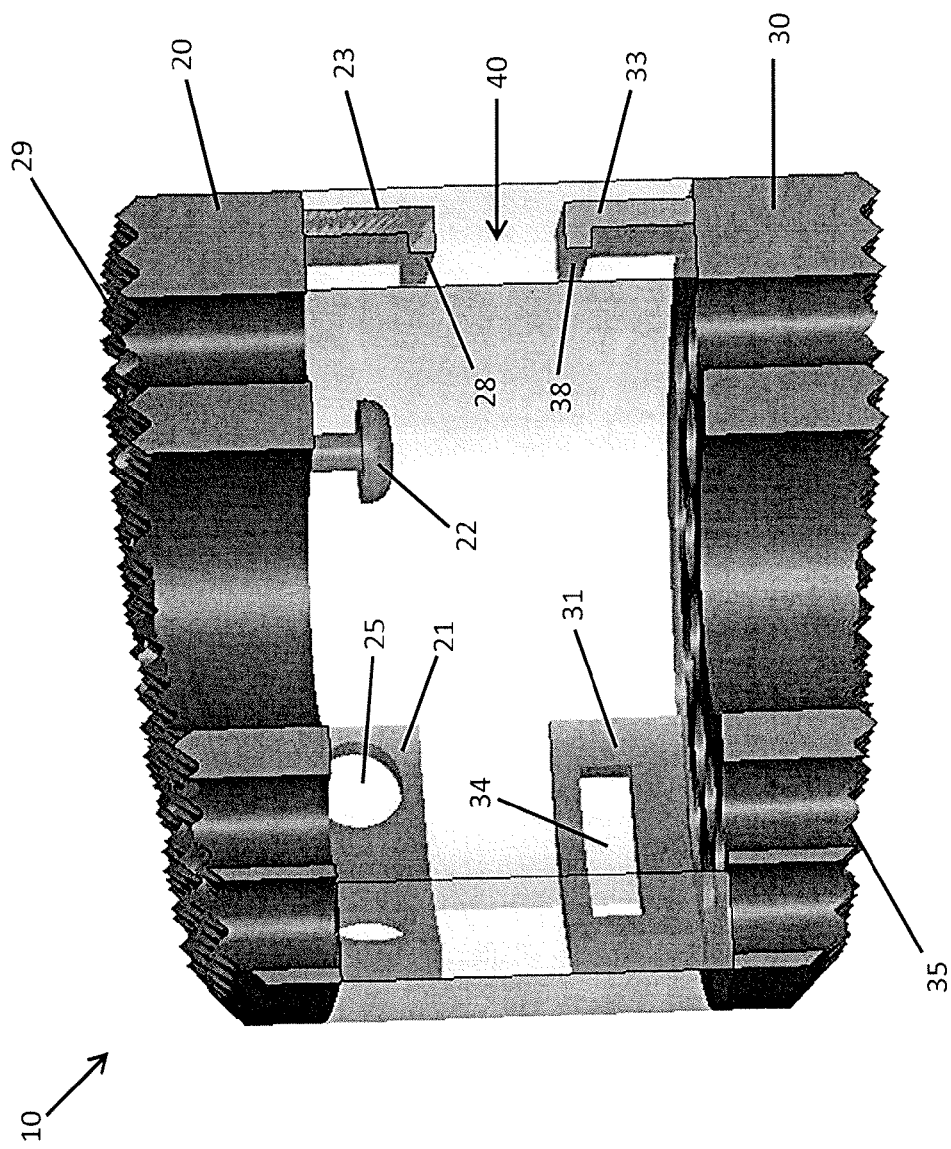
FIG. 3 shows an isometric cut-away view of an embodiment of the hybrid intervertebral disc spacer.

FIG. 3 shows a cut-away side/isometric view of the disc spacer 10, similar in orientation to the side view in FIG. 2. In addition to the wall protrusions 21, 31, and pin protrusions 22, 32 shown FIG. 2, the cut-away view of FIG. 3 shows a further wall protrusion which may be integrally formed with upper endplate 20 and lower endplate 30. More specifically, wall protrusions 23 and 33, integrally attached to upper endplate 20 and lower endplate 30, respectively, each have distal shelf 28 (at the end of wall protrusion 23) and 38 (at the end of wall protrusion 33). The distal shelf 28, 38 on wall protrusions 23, 33, similar to the pin protrusions 22, 32, provide both lateral stability and reduce the separation of either endplate 20, 30 from the spacer element 40. This is especially true given the preferred assembly method of back injection molding the spacer element between the endplates 20, 30. By back injection molding the spacer element 40, the plastic material is fully formed and in full contact with all surfaces of the wall and pin protrusions.

The cut-outs 24, 25, 34, 35 shown in wall protrusions 21 and 31 serve a similar purpose as the pin protrusions 22, 32, and wall protrusion 23, 33 (having distal shelves 28, 38). That is, in view of the back injection molding of the plastic spacer 40, the plastic material is fully formed in and through cut-outs 24, 25, 34, and 35. Although square or rectangular, and circular shapes are shown for the cut-outs 24, 25, 34, and 35, other shapes may be used in other embodiments and will be equally effective in providing lateral stability and reducing separation or delamination.

The endplates 20 and 30 are, in a preferred embodiment, manufactured from a porous biocompatible metal such as titanium or titanium alloy. Such metals exhibit significant bone apposition or fusion characteristics. Moreover, the porosity of the endplates 20 and 30, may be further tailored to promote ingrowth and fusion. Indeed, in another preferred embodiment, conventionally available ingrowth promoting material may be accommodated at the surfaces of the endplates 20, 30 that contact adjacent vertebra and also throughout holes or pores 27, 37 included in the endplates 20, 30 to help stimulate bone ingrowth and endplate fusion.

The plastic spacer 40 is made, in a preferred embodiment, from a radiolucent polymer-based material such as polyetheretherketone ("PEEK"), polyetherketone ("PEK"), polyetherketoneketone ("PEKK"), or fiber reinforced plastic, each of which have a e-modulus that is more similar to bone than metal. Moreover, given the e-modulus of PEEK, PEK, and PEKK, such plastics show optimal load absorption and load distribution when used as vertebral spacers. Indeed, PEEK, PEK and PEKK are materials that are often used in the manufacture of intervertebral spinal implants. Further, PEEK and other similar materials are almost entirely radiolucent and highly biocompatible. Being radiolucent, the use of PEEK as a material for the spacer 40, allows for precise positioning through use of X-ray equipment during and after insertion operation. Moreover, with the use of the metal endplates 20, 30, the exact position of the disc spacer 10 in relation to adjacent vertebrae using flouroscopy during the operation is easily achieved, without the use of X-ray markers.

As shown in FIGS. 1 through 6, the surfaces of the endplates 20, 30 may be formed with a highly uneven surface texture. The teeth or edges 29, 39 shown on endplates 20, 30 form a porous and substantially roughened surface texture of the endplate surfaces in contact with adjacent bone structure. The teeth 29, 39 provide excellent stability against migration or lateral movement or migration after placement of the disc spacer 10, as well as stability from flexion/extension loads, axial torsion loads, and lateral bending loads. The teeth 29, 39 also, given the biocompatible nature of the titanium metal, promote fusion of the bone with the endplates 20, 30 of spacer 10.

In other embodiments, the endplates 20, 30, or the surfaces of the endplates 20, 30 may be made of alternate materials such as a nitride, carbide, or oxide of a porous metal. Additionally, a porous cobalt/chromium alloys or stainless steel may be used as the metal. In another embodiment, appropriate sections of the endplates 20, 20 may be constructed of a porous radiolucent material with a comparatively thin layer of metal, such as titanium, deposited over that endplate section. Such a layer of metal may itself be crystalline or amorphous in structure.

Figure 4:
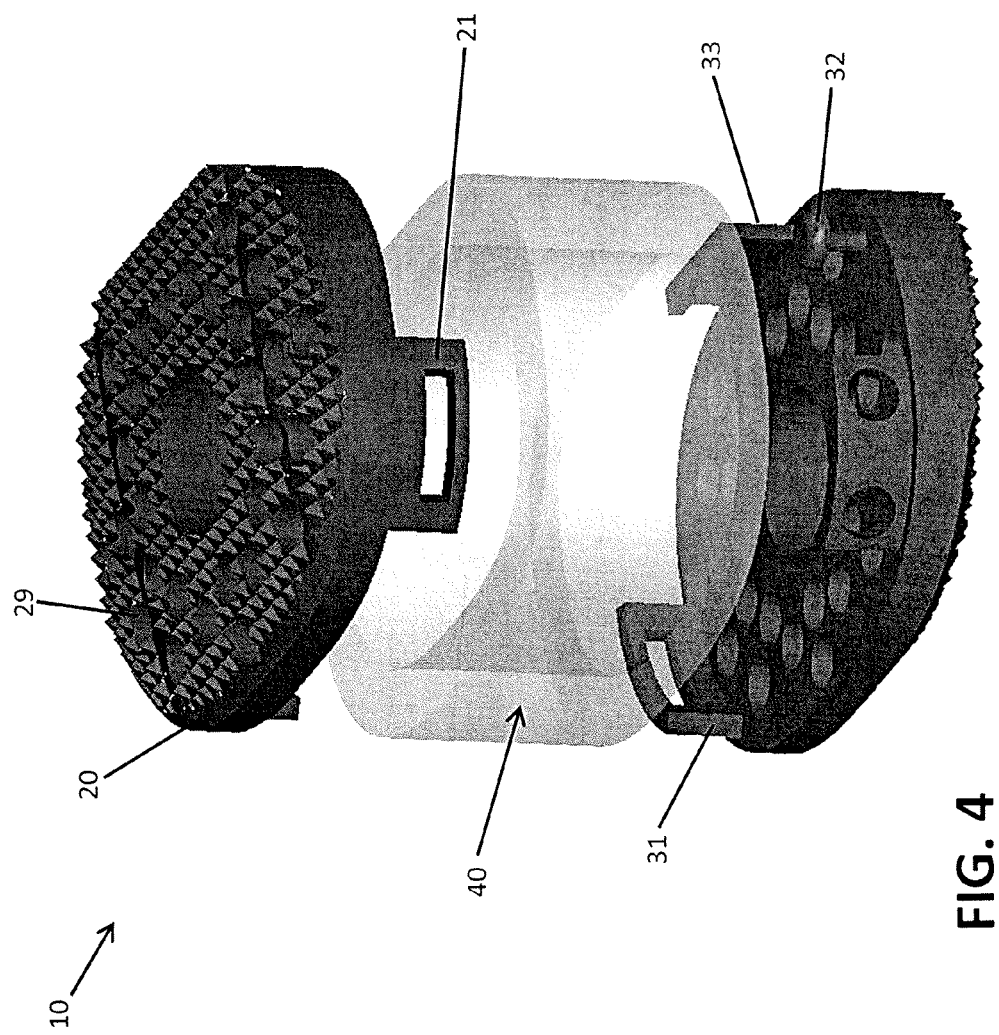
FIG. 4 shows an exploded isometric view of an embodiment of the hybrid intervertebral disc spacer.
Figure 5:
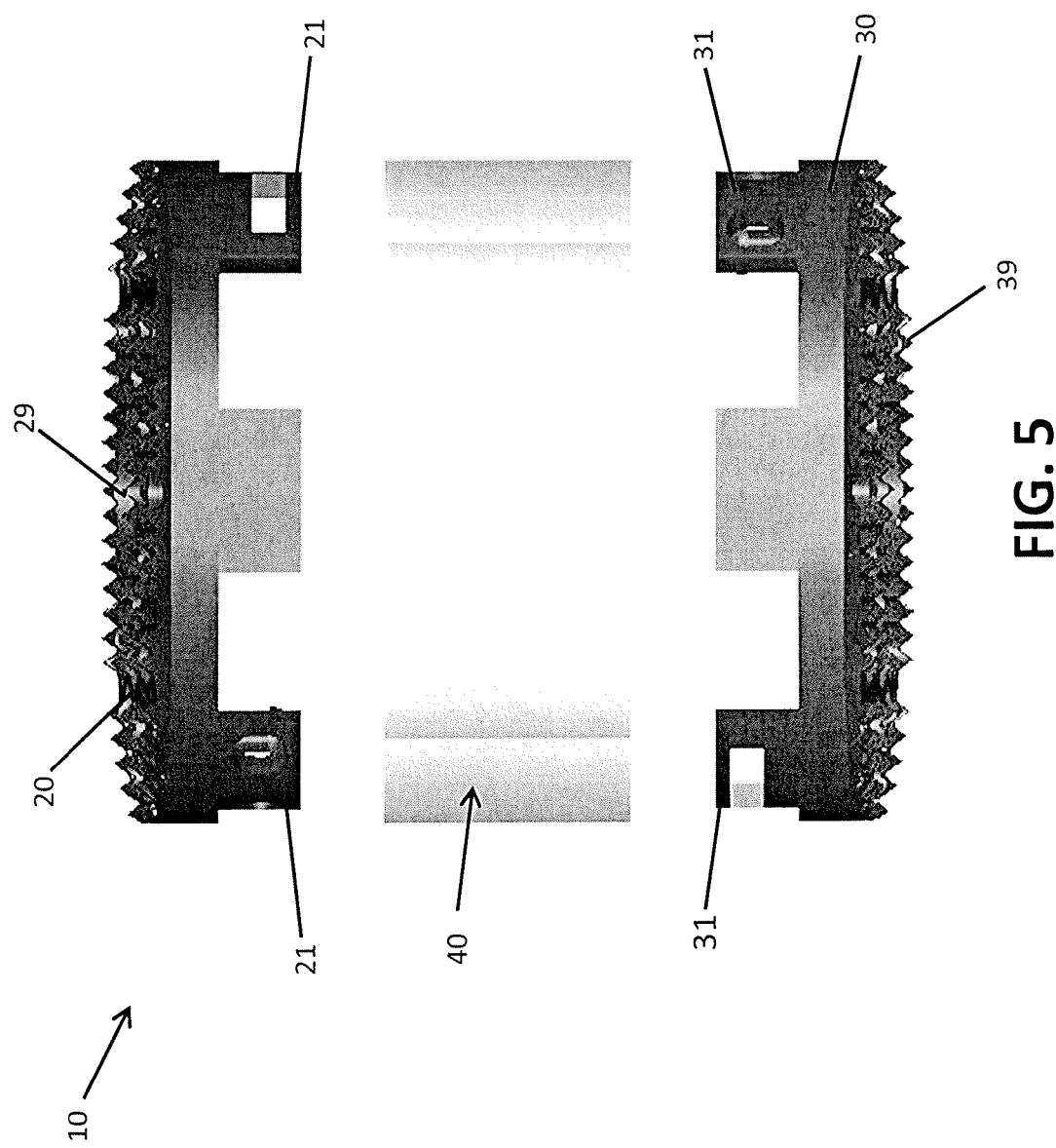
FIG. 5 shows an exploded side view of an embodiment of the hybrid intervertebral disc spacer.
Figure 6:
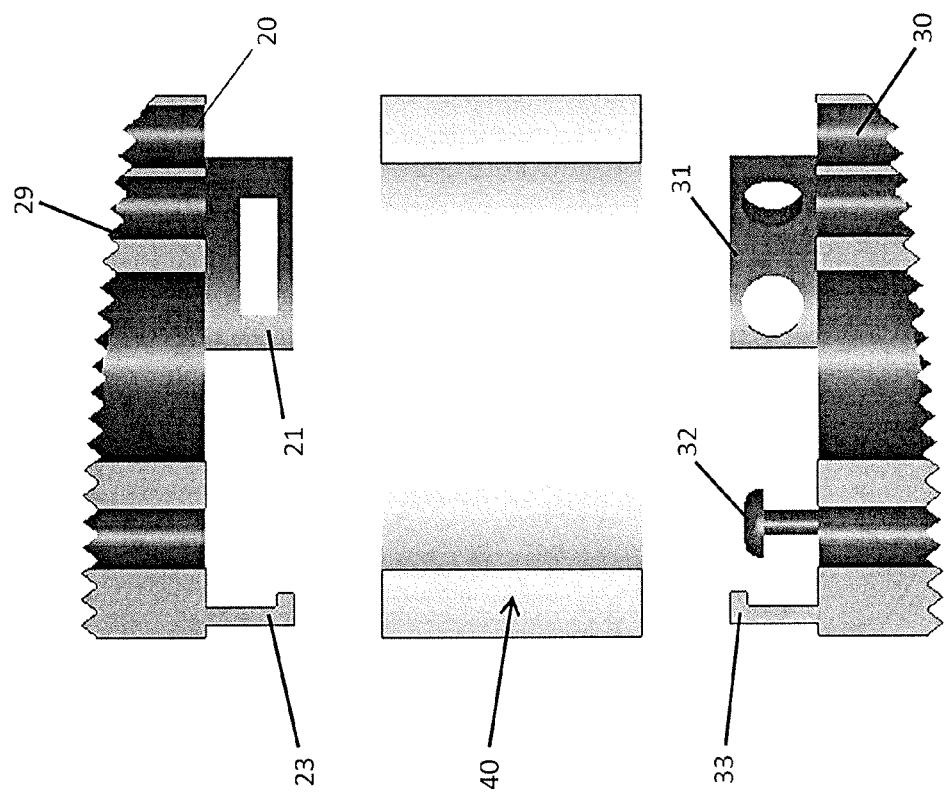
FIG. 6 shows an exploded cut-away side view of an embodiment of the hybrid intervertebral disc spacer.

FIG. 4 shows an isometric exploded view of a preferred embodiment of the present disc spacer 10. In this view, the cylindrical shape of the plastic spacer 40 is easier to see, in place between upper endplate 20 and lower endplate 30. Similarly, FIG. 5 shows a side view of the three elements, namely endplates 20 and 30, and plastic spacer 40, in an exploded view. Finally, FIG. 6 shows a similar cut-away side view of the same three elements of disc spacer 10.

Figure 7:
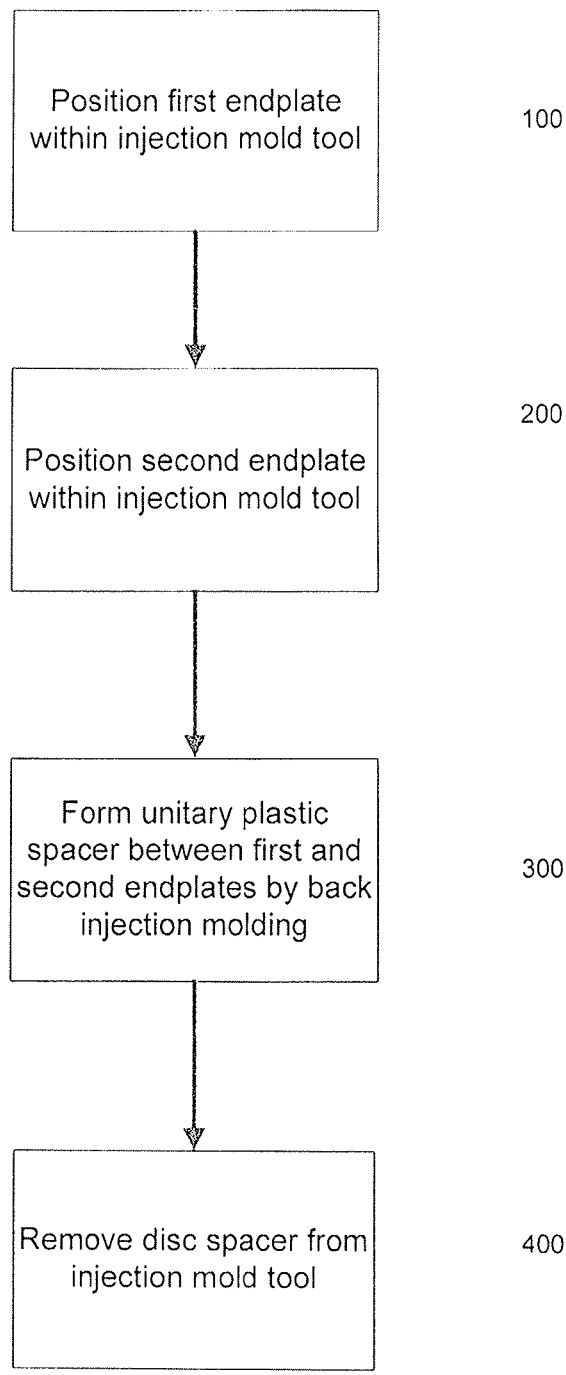
FIG. 7 shows an exemplary embodiment of process steps for the injection mold manufacturing of the hybrid intervertebral disc spacer.

As noted, one illustrative embodiment of the method of manufacturing the disc spacer 10 is through the use of injection, or injection back molding. FIG. 7 illustrates the basic steps of the method of precisely locating endplates 20 and 30 within an injection mold tool that provides the appropriate shape, size and form for the plastic spacer, and then injection molding the plastic material in between the two endplates, filling the form space between the two endplates 20, 30. The steps include first positioning the first endplate 100 within the injection mold tool; then positioning the second endplate 200 within the injection mold tool, creating between the two endplates the desired shape, size and form for the plastic spacer 40. Next the unitary plastic spacer 40 is formed between the two endplates by back injection molding 300 with the selected plastic material. Finally, the hybrid disc spacer 10 is removed 400 from the injection mold tool.

It should be readily apparent to those skilled in the art that the spacer 10 can be used between any adjacent bone portions, such as members at a joint, for example, in a void between such joint portions as might be developed by a fracture, through a procedure that removes bone as with a tumor. While the various embodiments and examples are contemplated for use with virtually any adjacent bone portions between which a spacer is required, the initial disclosure herein is directed towards spinal procedures wherein the spacer 10 is placed between adjacent vertebrae/joint members that make up the more generically referenced bone portions. As noted, the disclosed examples and embodiments are not however to be considered limiting as to effective uses of the spacer.

It is also understood that while the present disclosure has been to at least one embodiment for an invertebral disc spacer, the scope and coverage of preferred embodiments can be further modified and still be within the spirit and scope of this disclosure. This application is therefore intended to cover any variations, uses, or adaptations of the present disclosed embodiments using its general principles.

Further, this application is intended to cover such departures from the present disclosure as come within known or customary practice in the art to which this disclosure pertains and which fall within the limits of the appended claims. Further modifications and alternative embodiments of various aspects of the devices and methods will be apparent to those skilled in the art in view of this description.

Accordingly, this description is to be construed as illustrative only and is for the purpose of teaching those skilled in the art of the general manner of carrying out the present disclosure. Elements and materials may be substituted for those illustrated and described herein, parts and processes may be reversed, and certain features of the preferred embodiments may be utilized independently, all as would be apparent to one skilled in the art of having the benefit of this description. Changes may be made to the elements described herein, including shape of the spacer, without departing from the spirit and scope of the present disclosure as described in the following claims.

What is claimed is:

1. A hybrid spinal implant for positioning at an intervertebral space, comprising:
    a first end plate, configured for fitting within a disc space, wherein the first end plate comprises a first surface for engaging a first vertebral surface and a second surface opposite the first surface, wherein the second surface comprises at least one anchoring protrusion;
    a second end plate configured for fitting within a disc space, wherein the second end plate comprises a first surface for engaging a second vertebral surface and a second surface opposite the first surface, wherein the second surface comprises at least one anchoring protrusion, and wherein the second surface of the second end plate faces the second surface of the first end plate; and
    a unitary plastic spacer formed through injection molding between the first and second end plates such that the spacer completely surrounds all surfaces of the at least one anchoring protrusion of the first end plate and the at least one anchoring protrusion of the second end plate and such that the spacer is anchored to the first and second end plates respectively by each of the at least one anchoring protrusions;
    wherein the at least one anchoring protrusion of the first end plate comprises:
    a T-shaped pin protrusion extending away from the second surface of the first end plate toward the second surface of the second end plate; and
    a wall shaped protrusion extending away from the second surface of the first end plate and toward the second surface of the second end plate, the wall shaped protrusion having at least one cut-out formed therethrough.

2. The hybrid spinal implant device of claim 1, wherein the unitary plastic spacer is formed between the first and second end plates by back injection molding.

3. The hybrid spinal implant device of claim 1, wherein the first end plate and second end plate are manufactured from titanium.

4. The hybrid spinal implant device of claim 1, wherein the first end plate and second end plate are manufactured from a titanium alloy.

5. The hybrid spinal implant device of claim 1, wherein the first end plate and second end plate are manufactured with a surface made from titanium.

6. The hybrid spinal implant device of claim 1, wherein the unitary plastic spacer is manufactured from the group of materials consisting of PEEK, PEK, PEKK, and fiber reinforced plastic.

7. The hybrid spinal implant device of claim 1, wherein the plastic spacer is a unitary solid element.

8. The hybrid spinal implant device of claim 1, wherein the plastic spacer is a unitary ring-shaped cylinder.

9. A hybrid spinal implant for positioning at an intervertebral space, comprising:
    a first end plate, configured for fitting within a disc space, wherein the first end plate comprises a first surface for engaging a first vertebral surface and a second surface opposite the first surface, wherein the second surface integrally comprises a plurality of wall shaped protrusions;
    a second end plate configured for fitting within a disc space, wherein the second end plate comprises a first surface for engaging a second vertebral surface and a second surface opposite the first surface, wherein the second surface integrally comprises a plurality of wall shaped protrusions, and wherein the second surface of the second end plate faces the second surface of the first end plate;

a unitary ring-shaped plastic spacer formed through injection molding between the first and second end plates and anchored to the first and second end plates respectively by each of the plurality of wall shaped protrusions, the spacer being in full contact with all surfaces of the wall shaped protrusions of the first and second end plates;

wherein each of the plurality of wall protrusions of the first and second end plates is shaped as a wall extending away from the second surface of its respective end plate and toward the second surface of the other of the first and second end plates, each of the plurality of wall protrusions include at least one cut-out formed therethrough.

10. The hybrid spinal implant device of claim 9, wherein the first end plate and second end plate are manufactured from titanium.

11. The hybrid spinal implant device of claim 9, wherein the first end plate and second end plate are manufactured from a titanium alloy.

12. The hybrid spinal implant device of claim 9, wherein the first end plate and second end plate are manufactured with a surface made from titanium.

13. The hybrid spinal implant device of claim 9, wherein the unitary plastic spacer is manufactured from the group of materials consisting of PEEK, PEK, PEKK, and fiber reinforced plastic.

14. A hybrid bone implant for positioning within a bone structure cavity, comprising:

a first end plate, configured for fitting within a bone structure cavity, wherein the first end plate comprises a first surface for engaging a first bone surface and a second surface opposite the first surface, wherein the second surface comprises a plurality of wall shaped protrusions and a plurality of pin protrusions;

a second end plate configured for fitting within a bone structure cavity, wherein the second end plate comprises a first surface for engaging a second bone surface and a second surface opposite the first surface, wherein the second surface comprises a plurality of wall shaped protrusions and a plurality of pin protrusions, and wherein the second surface of the second end plate faces the second surface of the first end plate;

a unitary ring-shaped plastic spacer formed through injection molding between the first and second end plates such that the spacer is anchored to the first and second end plates respectively by each of the plurality of wall shaped protrusions and the plurality of pin protrusions and such that each of the plurality of wall protrusions and the plurality of pin protrusions is imbedded in the spacer;

wherein each of the plurality of wall shaped protrusions of the first and second end plates extends away from the second surface of its respective end plate and toward the second surface of the other of the first and second end plates, each of the plurality of wall protrusions include at least one cut-out formed therethrough.

* * * * *